US005543384A

United States Patent [19]

Brennan

[11] Patent Number: 5,543,384

[45] Date of Patent: Aug. 6, 1996

[54] METHOD OF MAKING PESTICIDE STICKER-EXTENDER

[75] Inventor: Joseph T. Brennan, Blytheville, Ark.

[73] Assignee: Terra International, Inc., Sioux City, Iowa

[21] Appl. No.: 439,173

[22] Filed: May 11, 1995

Related U.S. Application Data

[62] Division of Ser. No. 234,418, Apr. 28, 1994.

[51] Int. Cl.$^6$ .................... A01N 25/24

[52] U.S. Cl. .................... 504/116; 71/DIG. 1; 424/407

[58] Field of Search .................... 71/DIG. 1; 504/116; 424/407

[56] References Cited

U.S. PATENT DOCUMENTS

| | | | |
|---|---|---|---|
| 3,962,304 | 6/1976 | Matsushima et al. | 71/DIG. 1 |
| 4,334,914 | 6/1982 | Hiraga et al. | 71/100 |
| 4,659,492 | 4/1987 | Jahnke | 252/49.3 |
| 4,767,448 | 8/1988 | Nielson | 71/111 |
| 4,971,630 | 11/1990 | Skaptason | 71/117 |

FOREIGN PATENT DOCUMENTS

| | | |
|---|---|---|
| 56-86105 | 7/1981 | Japan . |

*Primary Examiner*—S. Mark Clardy
*Attorney, Agent, or Firm*—Joseph J. Previto

[57] ABSTRACT

A method of making a sticker-extender for pesticides comprising a first mixture comprising an anhydride, an acid and turpentine mixed with a second mixture comprising an isomeric alcohol and at least one amino alcohol, the first mixture comprising more than 50% of the total mixture. The anhydride is maleic anhydride and the acid is sulfuric acid. The amino alcohols are monoethanolamine, diethanolamine, triethanolamine and mono-isopropylamine.

11 Claims, No Drawings

METHOD OF MAKING PESTICIDE STICKER-EXTENDER

This is a division of pending U.S. application Ser. No. 08/234,418 filed Apr. 28, 1994.

The present invention relates to a pesticide product and more particularly to a sticker-extender for pesticide sprays.

BACKGROUND

Sticker-extenders for pesticide sprays have been known for a number of years and are used to extend the activities of pesticide sprays such as fungicides, herbicides and insecticides. A sticker-extender is intended to improve the performance of such pesticides by assisting to evenly spread the pesticide and form an elastic film to keep it in place. It has been found that existing pesticide spray additives sometimes do not extend the activity of the pesticide sprays for a very long period and sometimes do not help to spread the pesticides evenly over the entire plant or do not form a suitable elastic film to keep the pesticides in place. It also sometimes occurs that losses occur from rain, overhead irrigation and heavy dew and that losses also occur due to sunlight and evaporation.

Some existing sticker-extenders have poor canopy penetration and do not deposit the spray solutions deep into the crop foliage and others do not easily disperse in water to form emulsions.

It has been found that some sticker-extenders are more prone to fire and explosion and may be dangerous to use and store.

OBJECTS

The present invention is an improvement over existing pesticide spray additives and has for one of its objects the provision of an improved sticker-extender for extending the activity of pesticide sprays, such as insecticides, fungicides and herbicides.

Another object of the present invention is the provision of an improved sticker-extender which improves the performance of pesticides by helping to spread the pesticides evenly over the entire plant.

Another object of the present invention is the provision of an improved sticker-extender which improves the performance of pesticides by forming an elastic film to keep the pesticides in place.

Another object of the present invention is the provision of an improved sticker-extender which aids in preventing losses from rain, overhead irrigation and heavy dew.

Another object of the present invention is the provision of an improved sticker-extender which provides extra protection from losses due to sunlight and evaporation.

Another object of the present invention is the provision of an improved sticker-extender which aids in canopy penetration and helps deposit the spray solutions deep into the crop foliage.

Another object of the present invention is the provision of an improved sticker-extender which easily disperses in water to form an emulsion.

Other and further objects of the invention will be obvious upon an understanding of the illustrative embodiment about to be described, or will be indicated in the appended claims and various advantages not referred to herein will occur to one skilled in the art upon employment of the invention in practice.

DESCRIPTION OF INVENTION

The sticker-extender of the present invention is manufactured in a two stage process. The first stage produces an intermediate product hereinafter referred to as "Intermediate". The second and final stage produces the final product hereinafter referred to as "Final Product".

The intermediate preferably contains an anhydride made from an dibase acid, such as maleic anhydride, a strong acid such as sulfuric acid and turpentine preferably acintene P-AC turpentine. Preferably, the turpentine amounts to almost twice as much as the anhydride with the acid being in very small amounts.

Intermediate is preferably formulated as follows:

| INTERMEDIATE | |
|---|---|
| MALEIC ANHYDRIDE | 34.92% |
| SULFURIC ACID | 0.37% |
| ACINTENE P-AC TURPENTINE | 64.71% |
| TOTAL | 100.00% |

In order to make the final product, the Intermediate is added to a plurality of a number of alcohols such as an isomeric alcohol and a number of amino alcohols. Preferably, about 60% of the Final Product comprises Intermediate and the remainder comprises the said variety of alcohols.

The preferred formula which may be used in the preparation of the Final Product of the improved Sticker-Extender of the present invention is as follows:

| FINAL PRODUCT | |
|---|---|
| INTERMEDIATE | 60.40% |
| BUTANOL | 32.40% |
| MONOETHANOLAMINE (MEA) | 6.80% |
| DIETHANOLAMINE (DEA) | 2.00% |
| TRIETHANOLAMINE (TEA) | 5.90% |
| MONO ISOPROPYLAMINE | 2.50% |
| TOTAL | 100.00% |

The Intermediate is preferably manufactured by placing maleic anhydride into a reactor and heating it to about 170° C. After the maleic anhydride is melted, it is agitated in an agitator. Sulfuric acid is added to the agitator and cooling water is applied thereto. The turpentine is then added slowly over a two hour period. Temperature in the agitator is maintained between 170°–185° C. and any condensation may be returned by a condenser back to the reactor. Preferably, the temperature is kept above 167° to prevent turpentine buildup which may result in uncontrolled exothermic reaction. After all the turpentine has been added, the mixture is held at about 180°–185° C. for about two hours. The mixture is then cooled to about 40° C.

Following the above procedure, a batch of Intermediate was prepared. The kettle and all piping associated with the process are thoroughly cleaned. Cleaning was accomplished by applying a $N_2$ (Nitrogen) purge but any other well known cleaning step may be used. The kettle is then charged with about 4,900 lbs. of maleic anhydride. About 52 lbs. of $H_2SO_4$ (Sulfuric Acid) is then added. Cooling water is applied to the condenser and the kettle is set for total reflux. A water line is connected to the acid scrubber and a 2" vent line on the kettle to vent the kettle to the acid scrubber.

About 9080 lbs. (1268 gallons) of the turpentine is applied to the kettle at about 6 gpm (gallons per minute). Cold water is used to maintain the temperature at about 170° to 180° C. Preferably, the temperature should not go below 165° C. because the reaction may stop and unreacted raw materials may build up in the system causing runaway reaction when the kettle is heated back up to the reaction temperature. If the temperature falls below 165° C., the addition of Turpentine should be stopped and heat should be applied to the kettle to raise the temperature up to 170° and 180° before the Turpentine addition is resumed.

Once all the Turpentine is added, the reaction should be held at about 170° to 180° for about 2 hours. Thereafter, the batch is cooled to about 40° C. If it is determined that additional cook time is needed, the batch may be reheated to about 170° to 180° C. and held at that temperature for an additional 2 hours and thereafter allowed to cool to about 40° C.

The resulting Intermediate should have an amber color and the appearance of a homogeneous fluid.

In general, the Final Product is manufactured by placing the Intermediate into an agitator and starting the agitation. The Butanol, MEA, DEA and TEA are added preferably in that sequence while maintaining the temperature between 45° C. and 60° C. The Mono-Isopropyl Amine is then added preferably below the surface of the batch while the temperature is still below 60° C. The batch is mixed for about one hour and the Final Product should have the appearance of amber liquid with a pH of 7.0±0.5.

The Intermediate was added to the agitator and agitation of the batch is started. About 5192 lbs. (769 gallons) of Butanol is added to the batch. The agitator is heated to about 40° C. About 1576 lbs. of MEA is added to the batch. When the temperature reaches 50° C., the mixture may be cooled in any well known manner (such as through an oil recycle cooling system) and the MEA is continued to be added at a rate to hold the temperature below 60° C. Thereafter, about 464 lbs.of DEA is added and the temperature is kept below 60° C. by adjusting the rate at which the DEA is added. About 1367 lbs. of the TEA is then added and the temperature is kept below 60° C. by again adjusting the rate at which the TEA is added. About 570 lbs. of Mono Isopropylamine is added to the batch and again the temperature is kept below 60° C. by adjusting the rate at which it is added. Mix for about one hour to produce the Finished Product.

It will be seen that the present invention provides an improved sticker-extender which extends the activity of insecticides, fungicides and herbicide sprays which improves the performance of pesticides by helping to spread the pesticides evenly over the entire plant. The improved sticker-extender also improves the performance of pesticides by forming an elastic film to keep the pesticide in place and aids in preventing losses from rain, overhead irrigation, heavy dew, sunlight and evaporation. The improved sticker-extender aids in canopy penetration, helps deposit spray solutions deep into the crop foliage and disperses easily in water to form an emulsion.

As many and varied modifications of the subject matter of this invention will become apparent to those skilled in the art from the detailed description given hereinabove, it will be understood that the present invention is limited only as provided in the claims appended hereto.

The embodiments of the invention in which an exclusive property or privilege is claimed are defined as follows:

1. A method of making a sticker-extender for a pesticide which comprises the steps of mixing a first mixture and a second mixture together, the said first mixture comprising maleic anhydride, an acid and turpentine and the said second mixture comprising a butanol, MEA, DEA, TEA and Mono Isopropyl amine said first mixture being prepared by adding the acid to the anhydride and thereafter adding the turpentine, said first mixture comprising more than 50% of the total mixture.

2. A method as set forth in claim 1 wherein said turpentine is acintene P-AC turpentine and wherein said first mixture comprises maleic anhydride about 34.92%, sulfuric acid about 0.37%, and acintene P-AC turpentine about 64.71%, said second mixture being approximately 36.60% of the total mixture and comprises butanol about 22.40%, monoethanolamine about 6.80%, diethanolamine about 2.00%, triethanolamine about 5.90% and monoisopropylamine about 2.50%.

3. The method as claimed in claim 2 wherein said maleic anhydride is melted before the acid is added to it.

4. A method as claimed in claim 3 wherein the butanol, MEA, DEA and TEA are added to the first mixture in that order.

5. A method as claimed in claim 4 wherein thereafter the Mono Isopropylamine is added.

6. A method as claimed in claim 5 wherein the turpentine is added slowly for a period of about two hours.

7. A method as claimed in claim 6 wherein the temperature of the mixture is maintained between 170°–185° C.

8. A method as claimed in claim 7 wherein the first mixture is held at about 180°–185° C. for about two hours after the turpentine is added.

9. A method as claimed in claim 8 wherein the said first mixture is cooled to about 40° C.

10. A method as claimed in claim 9 wherein the temperature of the two mixtures is maintained below 60° C. during mixing.

11. A method as claimed in claim 10 wherein the two mixtures is mixed for about one hour.

* * * * *